United States Patent [19]

Hamilton

[11] Patent Number: 4,663,326

[45] Date of Patent: May 5, 1987

[54] PYRAZOLO[4,3-D]PYRIMIDINE-5,7-(4H,6H)DIONE OR -5-THIONE-7-ONE ANALOGS

[75] Inventor: Harriet W. Hamilton, Chelsea, Mich.

[73] Assignee: Warner-Lambert Company, Morris Plains, N.J.

[21] Appl. No.: 720,213

[22] Filed: Apr. 4, 1985

[51] Int. Cl.[4] .................... A61K 31/41; C07D 487/04
[52] U.S. Cl. ..................................... 514/258; 544/262
[58] Field of Search ......................... 544/262; 514/258

[56] References Cited

U.S. PATENT DOCUMENTS 4,031,218  6/1977  El-Antably ........................ 544/273
4,544,556  10/1985  Fedi ................................... 544/273

FOREIGN PATENT DOCUMENTS 52-05794  1/1977  Japan .

OTHER PUBLICATIONS

Robins, J. Amer. Chem. Soc., 78, p. 2418 (1956).
R. K. Robins, et al., J.O.C. 21(8), 833 (1956).
R. K. Robins, et al., JACS, 78, 2418 (1956).
R. F. Rose, J. Chem. Soc., 3448 (1952).
V. Papesh et al, J.O.C. 30(1) 199 (1965).
Ind. J. Chem. Sec. B, 21B (6) 585–6 (1982).

*Primary Examiner*—Robert J. Warden
*Assistant Examiner*—Robert Benson
*Attorney, Agent, or Firm*—Joan Thierstein

[57] ABSTRACT

Various novel analogs of pyrazolo[4,3d]pyrimidine-5,7-(4H,6H)diones and also 5-thione-7-ones, novel methods of synthesis therefor, compositions and uses are the present invention. For example, the novel 5,7-diones and 5-thione-7-ones are useful for stimulating the central nervous system reversing bronchoconstriction, and as cardiac stimulants cardiotonic agents.

16 Claims, No Drawings

PYRAZOLO[4,3-D]PYRIMIDINE-5,7-(4H,6H)DIONE OR -5-THIONE-7-ONE ANALOGS

BACKGROUND OF THE INVENTION

The present invention is various novel analogs of pyrazolo[4,3-d]pyrimidine-5,7-(4H,6H)-dione and also -5-thione-7-ones, novel methods of synthesis, compositions, and uses thereof. The use relates particularly to the analogs desirable affinity at A1 adenosine receptors, advantageous inhibition of phosphodiesterase and desirable central nervous system and cardiovascular activities. For example, the analogs stimulate the central nervous system, reverse bronchoconstriction, and act as cardiac stimulants and cardiotonic agents. The preferred method of use for the novel analogs of the present invention is for the treatment of bronchoconstriction and cardiac insufficiency.

R. K. Robins, et al, J.O.C. 21(8), 833 (1956) report a compound having the Formula X

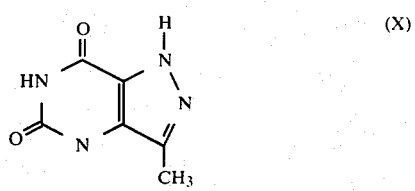

as a potential purine antagonist for chemotherapy but do not suggest the utility of the present invention. The same authors also report the chemical synthesis of a compound of Formula XX

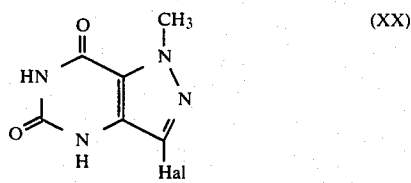

wherein Hal is chlorine or bromine by a reaction of the unsubstituted cyclized compound of Formula XXX

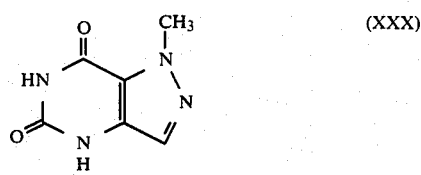

with dimethylsulfate in JACS, 78, 2418 (1956). The unsubstituted cyclized compound XXX is disclosed as isoxanthine by R. F. Rose in J. Chem. Soc., 3448 (1952). No utility is mentioned for either the compound of Formula XX or of Formula XXX. Further, synthesis for a compound having the Formula XL

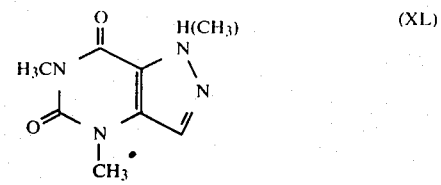

is given by V. Papesch, et al, in J.O.C. 30, (1) 199 (1965). UV comparisons of 3,4d versus 4,3d ring systems having the appropriate empirical formula appear in Ind. J. Chem. Sec B, 21B, (6), 585–6 (1982).

There is no teaching to the combination and location of the substituents on the 4,3-d ring system of the compounds of the present invention. Further, the compounds of the present invention cannot be made by any methods of the above discussed references.

Many references disclose oxipurinol type compounds which are distinguished by a different ring system, i.e., [3,4-d] ring system. The [3,4-d] ring systems do not teach the present invention having the [4,3-d] ring system. For example, Japanese 77 05.794 discloses 4-hydroxy and 4,6-dihydroxy-1H-pyrazolo[3,4-d]pyrimidine of Formula L

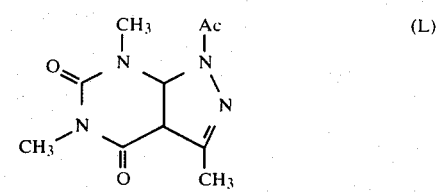

SUMMARY OF THE INVENTION

Accordingly, the present invention relates to a compound of Formula I

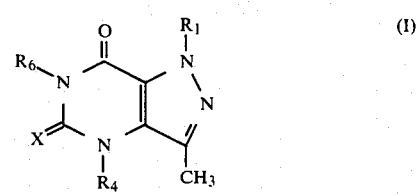

wherein X is oxygen or sulfur; $R_1$ is lower alkyl of from one to six carbons, inclusive, lower alkylene of from two to six carbons, hydroxyalkyl of from one to six carbons, inclusive, hydroxyalkylene of from two to six carbons, inclusive, aminoalkyl of from one to six carbons, inclusive, or aminoalkylene of from two to six carbons, inclusive; $R_4$ is hydrogen, lower alkyl of from one to six carbons, inclusive, lower alkylene of from two to six carbons, inclusive, hydroxyalkyl of from one to six carbons, inclusive, hydroxyalkylene of from two to six carbons, inclusive, aminoalkyl of from one to six carbons, inclusive, or aminoalkylene of from two to six carbons, inclusive; $R_6$ is hydrogen, lower alkyl of from one to six carbons, inclusive, alkylene of from two to six carbons, inclusive; hydroxyalkyl of from one to six carbons, inclusive, hydroxyalkylene of from two to six carbons, inclusive, aminoalkyl of from one to six carbons, inclusive, or aminoalkylene of from two to six carbons, inclusive; and the pharmaceutically acceptable salts thereof.

A preferred embodiment of the present invention is a compound of the Formula I wherein X is oxygen, and $R_1$, $R_4$, and $R_6$ are as defined above or a pharmaceutically acceptable salt thereof.

Another preferred embodiment of the present invention is a compound of the Formula I wherein X is oxygen, and $R_1$ is alkyl, $R_4$ and $R_6$ are as defined above or a pharmaceutically acceptable salt thereof.

A more preferred embodiment of the present invention is a compound of the Formula I wherein X is oxygen, and $R_1$ is ethyl, $R_4$ is hydrogen, and $R_6$ is defined above, or a pharmaceutically acceptable salt thereof.

A particular embodiment which is most preferred includes 1H-1-ethyl-3-methyl-6-propylpyrazolo[4,3-d]-pyrimidine-5,7-(4H,6H)dione or a pharmaceutically acceptable salt thereof.

The present invention also relates to a pharmaceutical composition comprising a therapeutically effective amount of a compound of the above Formula I with a pharmaceutically acceptable carrier and to a method of treating mammals, including humans, by administering to such mammals having a need for the treatment of dosage form of a compound of the Formula I as defined above.

In the compounds of the Formula I, the term lower alkyl of from one to six carbons includes a straight or branched alkyl group, such as, for example, methyl, ethyl, propyl, butyl, amyl, hexyl, and isomers thereof. The term alkylene of from two to six carbons, inclusive, includes a straight or branched alkylene group, such as for example, ethylene, propylene, butylene, amylene, hexylene and isomers thereof. Hydroxyalkyl of from one to six carbons includes alkyl as defined above, having a hydroxy substituent. Hydroxyalkylene of from two to six carbons includes alkylene as defined above having a hydroxy substituent. Likewise, aminoalkyl of from one to six carbons includes alkyl as defined above having an amino substituent and aminoalkylene of from two to six carbons includes alkylene as defined above having an amino substituent.

The compounds of Formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid and the like; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate salts, respectively.

DESCRIPTION OF THE PREFERRED EMBODIMENTS

The present invention particularly provides a compound according to Formula I as defined above, or a pharmacologically acceptable salt thereof; or an enantiomer or diastereomer of such compound.

Certain compounds of this invention, i.e., those with hydroxy-bearing or amino-bearing $R_1$, $R_4$, and $R_6$ may have asymmetric carbon atoms, and such compounds can exist as enantiomers or diastereomers. Thus, all names and representations of compounds as used herein shall include all such isomers and racemic mixtures thereof.

By virtue of the activity determined by the test procedures as described below the compounds of Formula I are useful in treating symptoms in mammals including humans associated with desirable effects recognized as stimulation of the central nervous system, reversing bronchoconstriction, stimulation of the cardiac system, action of cardiotonic agents. A physician or veterinarian of ordinary skill readily determines a subject who is exhibiting symptoms responding to such desirable effects. Regardless of the route of administration selected, the compounds of the present invention are formulated into pharmaceutically acceptable dosage forms by conventional methods known to the pharmaceutical art.

The compounds can be administered in such oral unit dosage forms as tablets, capsules, pills, powders, or granules. They also may be administered rectally, vaginally in such forms as suppositories or bougies: they may also be introduced parenterally (e.g., subcutaneously, intravenously, or intramuscularly), using forms known to the pharmaceutical art. They are also introduced directly to an affected area, (e.g., by inhalation). In general, the preferred route of administration is orally.

An effective quantity of the compound is employed in treatment. The dosage regimen for preventing or treating the symptoms as described above by the compounds of this invention is selected in accordance with a variety of factors including the type, age, weight, sex, and medical condition of the mammal, the severity of the symptoms, the route of administration, and the particular compound employed. An ordinarily skilled physician or veterinarian will readily determine and prescribe the effective amount to prevent or arrest the progress of the condition having the symptoms as described herein. In so proceeding, the physician or veterinarian could employ relatively low dosages at first, subsequently increasing the dose until a maximum response is obtained.

Daily dosages of the compounds of the invention are ordinarily in the area of 0.1 mg/kg up to at least 100 mg/kg per dose orally, preferably one to 50 mg/kg orally and are given from one to four times daily or as needed. When other forms of administration are employed equivalent doses are administered. When dosages beyond 200 mg/kg are employed, care should be taken with each subsequent dose to monitor possible toxic effects. When other forms of administration are employed equivalent doses are administered.

Generally, the compounds of Formula I are conveniently synthesized in the methodology shown in Scheme I.

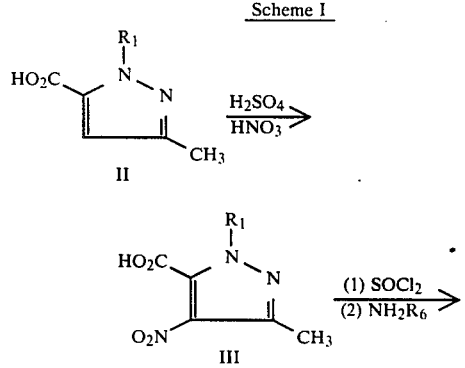

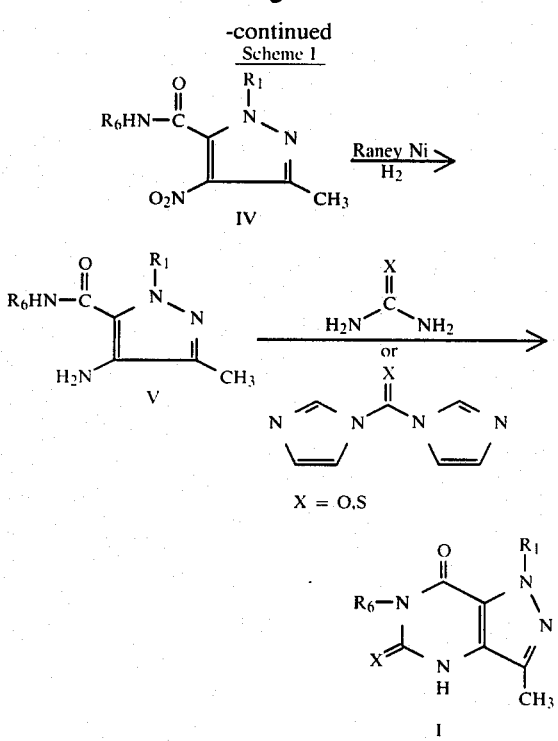

Thus, the known compound of Formula II is treated with sulfuric acid and fuming nitric acid at elevated temperature of from about 80° to 100° C. to effect nitration and give the compound of Formula III. The amide of Formula IV is conveniently synthesized from the carboxylic acid in a standard manner, e.g., treatment with thionyl chloride in an inert solvent, or neat, at 0° C., followed by treatment with the appropriate primary amine, either in organic solvent or as an aqueous solution. The nitro compound of Formula V is obtained as the product of catalytic hydrogenation of the compound of Formula IV using Raney nickel as a catalyst, in a suitable solvent such as an alcohol, or an alcohol and THF. Cyclization to the dione can be realized by heating a compound of Formula V as a neat melt with urea or thiourea, followed by pouring over ice; it can also be cyclized in solution with urea or thiourea at an elevated temperature. It is also possible to substitute carbonyldiimidazole or thiocarbonyldiimidazole as a cyclization agent to obtain compounds of Formula I.

PHARMACOLOGICAL EVALUATION

The compounds of Formula I have been found to possess affinity for adenosine receptors (designated $A_1$ for convenience).

ADENOSINE RECEPTOR BINDING-$A_1$ RECEPTOR AFFINITY (RBA1)

Preparation of Membranes

Whole brain minus cerebellum and brainstem from male Long Evans rats (150-200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000×g (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM [$^3$H]-$N^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding ($IC_{50}$) was determined by nonlinear computer curve fit. The Scatchard plot was calculated by linear regression of the line obtained by plotting the amount of radioligand bound (mmoles/gram of tissue) versus [bound radioligand/free radioligand]. Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the log of the [bound radioligand/($B_{max}$−bound radioligand)]. The maximal number of binding sites ($B_{max}$) was calculated from the Scatchard plot.

The $IC_{50}$ values (nM) for adenosine $A_1$ affinity is reported in Table 1.

TABLE 1

| Example | Receptor Binding RBA-1 (nM) |
|---|---|
| 1 | 11000 |
| 2 | 19300 |
| 3 | 5880 |
| 4 (Test 1) | 1040 |
| (Test 2) | 1520 |
| 5 (Test 1) | 458 |
| (Test 2) | 992 |
| (Test 3) | 378 |
| (Test 4) | 401 |
| 6 | 2530 |

PHOSPHODIESTERASE (PDE) INHIBITION

Isolation of Multiple Molecular Forms of Phosphodiesterase

The method of Thompson, et al (Thompson, W. J., Terasaki, W. L., Epstein, P. M., Strada, S. J., Adv. Cyclic Nucleotide Res., 10:69-92, 1979), with minor modifications, was used to isolate phosphodiesterases from vascular smooth muscle. Bovine coronary arteries (right, anterior descending, and left circumflex arteries) from hearts obtained from a local slaughterhouse were used for these studies. Arteries from two hearts were used for each isolation. Hearts were kept on ice and the arteries were dissected within two hours after the animals were sacrificed. After removing all fat and connective tissue, the arteries were everted, cut into cubes with a single edge razor blade and homogenized with a Brinkman Polytron three times at a rheostat setting of 10.0 in four volumes of the PDE isolation buffer (10 mM Tris-HCl/pH 7.5, 2 mM MgCl$_2$, and 1 mM dithiothreitol). The resulting homogenate was sonicated (30 sec/ml homogenate) and then centrifuged at 30,000×g for 20 minutes. This and all subsequent procedures were performed at 4° C. The resulting supernatant was filtered through four layers of gauze, and applied to a DEAE-cellulose column (30×1.5 cm), prepared as described by Cheung (Cheung, W. Y., *Biochim. Biopphys. Acta*, 191:303-315, 1969), and equilibrated with freshly prepared 70 mM sodium acetate/5 mM 2-mercaptoethanol (pH 6.5). The column was then washed with 2-3 bed volumes of sodium acetate/2-mercaptoethanol, after which the phosphodiesterases were eluted from the column using a continuous 70-1,000 mM sodium acetate gradient (pH 6.5, containing 5 mM 2-mercaptoethanol; total volume 400 ml). The flow rate was approximately equal to 25 ml/hr. Eight ml fractions were collected and assayed for cyclic AMP- and cyclic GMP-phosphodiesterase activity in the presence and absence of 0.1 units of calmodulin and 10 mM CaCl$_2$. Appropriate fractions were pooled and dialyzed against 70 mM sodium acetate/5 mM 2-mercaptoethanol for 20 hours.

Following complete separation, the combined phosphodiesterase fractions were concentrated to 14% of the original volume using an Amicon ultrafiltration cell fitted with a UM-10 membrane, according to the method of Wells, et al (Wells, J. N., Baird, C. E., Wu, Y. J., Hardman, J. G., *Biochim. Biophys. Acta*, 384:430-442, 1975). Following concentration, the protein was then diluted to 65% with ethylene glycol monoethyl ether, and stored at −20° C. No significant change in hydrolytic activity was observed with storage up to six weeks.

Measuring Phosphodiesterase Activity

Phosphodiesterase activity was measured as described previously (Weishaar, P. E., Quade, M., Boyd, D., Schenden, J., Mark, S. S., Kaplan, H. R., *Drug Devel. Res.*, 3:517-534, 1983), in a reaction medium containing 40 mM Tris-HCl (pH 8.0), 5 mM MgCl and 4 mM 2-mercaptoethanol. Unless otherwise noted, the concentration of substrate ($^3$H-cyclic AMP or $^3$H-cyclic GMP) was 1.0 μM. All agents examined were dissolved in dimethyl sulfoxide (DMSO). Final concentration of the reaction medium was either 2.5% (cardiac and platelet studies) or 1.25% (smooth muscle studies). This concentration of DMSO produced an approximately 10% inhibition of enzyme activity. IC$_{50}$ values (concentration which produced 50% inhibition of substrate hydrolysis) was determined from concentration-response curves, in which concentrations ranged from $10^{-7}$ to $10^{-4}$ for the more potent inhibitors and $10^{-5}$ to $10^{-3}$M for the less potent inhibitors (half-log increments). Three to four such concentration-response curves were generated for each agent, generally using different enzyme preparations for each concentration-response.

TABLE 2

| | | | PDE Inhibition | | | | |
|---|---|---|---|---|---|---|---|
| | | | Type 1 Phosphodiesterase | | Type 2 Phosphodiesterase | | Type 3 Phosphodiesterase |
| Example | Tissue or Cell Type | Conc. Tested | % Inhibition of 3H-cAMP Hydrolysis | % Inhibition of 3H-cGMP Hydrolysis | % Inhibition of 3H-cAMP Hydrolysis | % Inhibition of 3H-cGMP Hydrolysis | % Inhibition of 3H-cAMP Hydrolysis |
| 1 | Smooth muscle | 1 × 10$^{-5}$ M | N(2)* | N(2) | — | — | N(2) |
| 2 | Smooth muscle | 1 × 10$^{-5}$ M | N(2) | N(2) | — | — | B(2) |
| 3 | Cardiac muscle | 1 × 10$^{-4}$ M | B(1) | B(1) | B(1) | B(1) | A(1) |
| 4 | Cardiac muscle | 1 × 10$^{-4}$ M | A(1) | A(1) | A(1) | A(1) | A(1) |
| 5 | Cardiac muscle | 1 × 10$^{-4}$ M | A(1) | A(1) | A(1) | A(1) | B(1) |
| 6 | Cardiac muscle | 1 × 10$^{-4}$ M | A(1) | A(1) | B(1) | A(1) | A(1) |
| 7 | Cardiac muscle | 1 × 10$^{-4}$ M | C(1) | N(1) | B(1) | B(1) | C(1) |
| 8 | Cardiac muscle | 1 × 10$^{-4}$ M | B(1) | B(1) | A(1) | A(1) | A(1) |
| 9 | Cardiac muscle | 1 × 10$^{-4}$ M | A(1) | A(1) | A(1) | A(1) | A(1) |

*Numbers in parentheses refer to the number of times the agent was tested.
Ratings:
N = 0-20% inhibition at 1 × 10$^{-5}$ M
C = 21-35% inhibition at 1 × 10$^{-5}$ M
B = 36-55% inhibition at 1 × 10$^{-5}$ M
A = 56-100% inhibition at 1 × 10$^{-5}$ M
NJ = No Judgement
HRT = Cardiac and Platelet
SMUS = Smooth Muscle The compounds of this invention may be determined to have antiallergy activity by a standard laboratory means employing the bronchodilator test (BCA) readily accepted as a standard for antiallergy activity, which is described in Siegmund, H. O., et al (J. Pharmacol. and Exptl., 90:254, 1949 and Herxheimer, H., J. Physiol., 117: 252-255, 1952). Thus, antiallergy activity was found for compounds of this invention by this BCA test using Hartley Guinea Pigs by the procedures as described below.

Procedure

Naive (BCA) pigs are exposed to spasmogen for ten minutes by means of a De Vilbiss number 40 nebulizer positioned at the back of a closed, six unit plexiglas chamger (19×12.5×9"). Air flow is adjusted to give a pressure of 10 lbs/in; six animals per treatment are averaged, and the mean value for compound treated animals is compared to that for animals treated with vehicle. Guinea pigs that do not collapse are removed from the chamber after ten minutes and the maximum score of ten is recorded. Test compounds (25 mg/kg, IP) are given 15 minutes before exposure to spasmogen.

The spasmogen may be acetylcholine chloride (0.3%), histamine (0.1%), methacholine chloride (Mecholyl) (0.1%) or serotonin creatinine sulfate. Each nebulizer dispenses 0.2 cc/minute.

TABLE 4

BCA Results
(The agent in each case was histamine)

| Example | Dose (mg/kg) | Ratings |
|---------|--------------|---------|
| 1 | 50 | A |
| 3 | 50 | A |
| 4 | 50 | A |
| 5 | 50 | A |
| 6 | 50 | A |
| 7 | 50 | A |
| 8 | 50 | A |

Ratings: A = Active

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

TEST FOR IN VIVO MYOCARDIAL INTROPIC ACTIVITY IN ANESTHETIZED DOG (CVAD)

This screen consists of determining the effects of increasing intravenous doses of compound on mycardial contractility (dP/dt max of left ventricular blood pressure), heart rate, and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 to 1.0N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 mg/kg over a period of one minute.

When tested by the above-described Anesthetized Dog Procedure, the compounds of the present invention, for example, compound Ia of Example 1, when administered intravenously at about 0.01 to 0.31 mg/kg cause dose related significant increases in cardiac contractility with only low or minimal changes in heart rate and a moderate reduction in blood pressure. Accordingly, the compounds of the present invention are also useful as antihypertensive agents.

The results are summarized in the following table.

TABLE 5

| Example | Dose (mg/kg) | Percent Change Myocardial Contractility | Heart Rate | Blood Pressure |
|---------|--------------|-----------------------------------------|------------|----------------|
| 1 | 0.00 | | | |
| | 0.10 | 5 | 1 | 1/1 |
| | 0.31 | 13 | 1 | 1/−1 |
| | 1.00 | 41 | 5 | 0/−2 |
| | 3.10 | 90 | 15 | −2/−4 |
| 2 | 0.00 | | | |
| | 0.00 | | | |
| | 0.10 | 5 | 3 | −1/−1 |
| | 0.30 | 8 | 2 | −3/−4 |
| | 1.00 | 13 | −1 | −2/−4 |
| | 3.10 | 45 | 5 | −6/−9 |

The following Preparations and Examples will further illustrate the invention without limiting it thereto.

PREPARATION 1

1,3-Dimethyl-4-nitropyrazol-5-carboxylic acid

One-hundred and twelve grams concentrated sulfuric acid is added to 42 ml 90% nitric acid at 70°–80° C. To this 39 grams 1,3-dimethylpyrazole-5-carboxylic acid is added in portions over one hour such that temperature does not go over 90° C. After 2.5 hours the reaction mixture was cooled and poured over ice. The resulting percipitate was filtered, dried, and recrystallized in ethanol, to produce 1,3-dimethyl-4-nitropyrazol-5-carboxylic acid having mp 141°–142° C.

PREPARATION 2

1,3-Dimethyl-4-nitropyrazol-5-carboxamide

Forty grams of 1,3-dimethyl-4-nitropyrazole-5-carboxylic acid as prepared in Preparation 1 was stirred with 200 ml thionyl chloride at reflux for 3.5 hour. The excess thionyl chloride was distilled away under reduced pressure. The resulting oil was dissolved in acetone and added to icy ammonium hydroxide with stirring. The resulting precipitate was filtered and dried to give the product, 1,3-dimethyl-4-nitropyrazol-5-carboxamide having mp 154°–158° C.

PREPARATION 3

1,3-Dimethyl-4-aminopyrazole-5-carboxamide

Fifty grams of 1,3-dimethyl-4-nitro-pyrazole-5-carboxamide as prepared in Preparation 2 is dissolved in methanol, 2 g 50% of Raney nickel is added, and the compound is reduced under a hydrogen atmosphere until a 8.15 pound drop in pressure noted. The reaction mixture was filtered, the filtrate concentrated, and the crude material recrystallized in ethyl acetate to yield the product, 1,3-dimethyl-4-amino-pyrazol-5-carboxamide mp 154°–155° C.

EXAMPLE 1

1,3-Dimethylpyrazolo[4,3-d]pyrimidine-5,7-(4H,6H)dione

Ten grams of urea was melted. To this was added 5 g (32 mmol) 1,3-dimethyl-4-aminopyrazolo-5-carboxamide as prepared in Preparation 3, with rapid stirring. After two hours, this was poured into ice water, and the resulting white percipitate filtered. This was recrystallized in 1:1 ethanol/water to give the product, 1,3-dimethylpyrazolo[4,3-d]pyrimidine-5,7-(4H, 6H)dione having mp 355°–357° C.

Analysis as: $C_7H_8N_4O_2$ (180.17): Calcd: C, 46.67; H, 4.48; N, 31.20. Found: C, 46.59; H, 4.34; N, 31.15.

The starting material for Example 1 was made from 1,3-dimethyl-4-nitro-pyrazolo-5-carboxamide of Formula IVa (U.S. Pat. No. 3,553,209 and U.S. Pat. No. 4,469,868) by reduction in the usual manner with Raney nickel to yield 1,3-dimethyl-4-amino-pyrazolo-5-carboxamide of Formula Va, mp 154°–156° C.

The starting material for Example 2 and 3 was made in an analogous manner from 1-ethyl-3-methyl-4-nitro-pyrazolo-5-carboxamide of Formula IVb to give 1-ethyl-3-methyl-4-amino-pyrazolo-5-carboxamide of Formula Vb, mp 140°–142° C.

EXAMPLE 2

1-Ethyl-1,4,5,6-tetrahydro-3-methyl-pyrazolo[4,3-d]pyrimidine-5-thione-7-one

Five grams of 1-ethyl-3-methyl-4-aminopyrazolo-5-carboxamide was dissolved in anhydrous THF. To this was added 5.3 g thiocarbonyldiimidazole (one equivalent, dissolved in THF/chloroform) dropwise. The solution was stirred under nitrogen for 18 hours. The resulting percipitate was filtered, dried, and recrystallized in 95% ethanol to yield the product, 1-ethyl-3-methylpyrazolo[4,3-d]pyrimidine-5-thione-7-one mp 297°–300° C.

Analysis as: Calcd: C, 45.70; H, 4.79; N, 26.65; S, 15.25. Found: C, 45.65; H, 5.04; N, 26.53; S, 15.45.

EXAMPLE 3

1-Ethyl-3-methyl-1H-pyrazolo[4,3-d]pyrimidine-5,7(4H,6H)dione

The compound was made as in Example 1 using 10 g urea and 5 g 1-ethyl-3-methyl-4-amino-pyrazolo-5-carboxamide. The crude solid was recrystallized in absolute ethanol to give 1-ethyl-1,4,5,6-tetrahydro-3-methylpyrazolo[4,3-d]pyrimidine-5,7-(4H,6H)dione having mp 280°–282° C.

Analysis as: $C_8H_{10}N_4O_2$ (194.20): Calcd: C, 49.48; H, 5.19; N, 28.85. Found: C, 49.43; H, 5.16; N, 28.95.

EXAMPLE 4

1-Ethyl-3-methyl-6ethyl-1H-pyrazolo[4,3-d]pyrimidine-5,7-[4H,6H]dione

Two and 0.98 grams of 1-ethyl-3-methyl-4-aminopyrazolo-5-N-ethyl carboxamide was dissolved in 30 ml anhydrous THF at 40° under nitrogen; 2.46 g carbonyldiimidazole (one equivalent) was added in a single portion as a THF suspension. The mixture was heated at 80° for 36 hours, then filtered while hot. The filtrate was concentrated. The resulting solid was put into 150 ml 0.1N KOH, filtered, then the filtrate taken to pH 10.4 with acetic acid. The resulting white precipitate was filtered, yielding the product, 1-ethyl-3-methyl-6-ethylpyrazolo[4,3-d]pyrimidine-5,7-[4H,6H]dione having mp 208°–209° C.

Analysis as: $C_{10}H_{14}N_4O_2$ (222.25): Calcd: C, 54.04; H, 6.35, N, 25.21. Found: C, 54.03; H, 6.49; N, 25.08.

The starting material for Example 4 was made in the following manner:

Two-hundred grams of 1-ethyl-3-methyl-4-nitropyrazolo-5-carboxylic acid having the Formula 3 wherein $R_1$ is ethyl, was suspended in toluene. Two-hundred and eight grams of phosphorus pentachloride was added in small portions with stirring and the stirring continued for 14 hours. After the addition was complete the resulting 1-ethyl-3-methyl-4-nitropyrazolo-5-carbonyl chloride was used as a crude material.

The resulting 1-ethyl-3-methyl-4-nitropyrazolo-5-carbonyl chloride was added to a stirred solution of 70% aqueous ethylamine. Ice water was added after the addition was complete, and the pale yellow solid collected as a compound having the Formula IV wherein $R_1$ is ethyl, and $R_6$ is also ethyl, mp 115°–116° C. This material was hydrogenated using Raney nickel as a catalyst to give a compound of Formula V wherein $R_1$ and $R_6$ are ethyl.

Analysis as: $C_9H_{14}N_4O_3$ (226.34): Calcd: C, 47.78; H, 6.24; N, b 24.76. Found: C, 47.97; N, 6.26; N, 24.67.

EXAMPLE 5

1H-1-Ethyl-3-methyl-6-propyl-pyrazolo[4,3-d]pyrimidine-5,7-[4H,6H]dione

The product was prepared as in Example 4 using 2.57 g 1-ethyl-3-methyl-4-aminopyrazolo-5-N-propylcarboxamide and 1.98 g carbonyldiimidazole, mp 205°–206° C.

Analysis as: $C_{11}H_{16}N_4O_2$ (236.28): Calcd: C, 55.92; H, 6.8; N, 23.71. Found: C, 55.83; H, 6.97; N, 23.62.

The starting material for Example 5 was prepared in an analogous manner to the starting material for Example 4, by treating the carbonyl chloride with 25 ml n-propylamine in 75 ml water to give the nitro amidopyrazole of Formula V wherin $R_1$ is ethyl and $R_6$ propyl having the mp 100°–101° C., followed by catalytic reduction.

Calcd: C, 49.99; H, 6.71; N, 23.32. Found: C, 49.31; H, 6.77; N, 22.49.

EXAMPLE 6

1-Ethyl-3,6-dimethyl-1H-pyrazolo-[4,3-d]pyrimidine-5,7-[4H,6H]dione

Example 6 was prepared as described in Example 4 using 2.27 g 1-ethyl-3-methyl-4-amino-pyrazole-5-N-methyl-carboxamide and 2.02 g carbonyldiimidazole, mp 263°–264° C.

Analysis as: $C_9H_{12}N_4O_2$ (208.22): Calcd: C, 51.92; H, 5.81; N, 26.91. Found: C, 51.97; H, 5.78; N, 27.25.

The starting material for Example 6 was prepared in an analogous manner for the starting material for Example 4 by treating a compound of Formula III wherein $R_1$ is ethyl with 40% aqueous methylamine, followed by catalytic reduction.

EXAMPLE 7

1,3,4,6-tetramethyl-1H-pyrazolo[4,3-d]pyrimidine-5,7-[4H,6H]dione

Sodium hydride (0.62 g, 26 mmol) as a suspension in dimethyl formamide (DMF) (100 ml) was treated at once with the dioxo compound, from Example 1, (2.2 g, 12.2 mmol). This solution was warmed to 80° C. and stirred, under $N_2$ atmosphere, for one hour. This solution was then treated, at once, with methyl iodide (5.0 g, 35 mmol).

This solution is then stirred at 80° C., for 24 hours and the DMF removed in vacuo to give a dark semi-solid. The semi-solid was treated with water and the precipitate collected by filtration. The solid was washed with hexane (500 ml) and dried in vacuo at room temperature, overnight, yielding 1.5 g of 1,3,4,6-tetramethyl-1H-pyrazolo[4,3-d]pyrimidine-5,7-[4H,6H]dione (59%); mp 210°-211° C.

Analysis as: ($C_9H_{12}N_4O_2$): Calcd: C, 51.92; H, 5.77; N, 26.92. Found: C, 52.21; H, 5.74; N. 26.72.

EXAMPLE 8

4,6-Diethyl-1,3-dimethyl-1H-pyrazolo[4,3-d]pyrimidine-5,7-[4H,6H]dione

The title compound was prepared as in Example 7 using the dioxo compound, from Example 1, (2.2 g, 12 mmol), sodium hydride (0.62 g, 26 mmol), and ethyl iodide (5.5 g, 35 mmol), yield was 0.9 g of 4,6-diethyl-1,3-dimethyl-1H-pyrazolo[4,3-d]pyrimidine-5,7-[4H,6H]dione (32%); mp 95.5°-98° C.

Analysis as: $C_{11}H_{16}N_4O_2$: Calcd: C, 55.93; H, 6.78; N, 23.73. Found: C, 55.71; H, 6.91; N, 23.73.

EXAMPLE 9

1,3-dimethyl-4,6-dipropyl-1H-pyra-3-zolo[4,3-d]pyrimidine-5,7-[4H,6H]dione

Sodium hydride (0.86 g, 39 mmol) as a suspension in DMF (100 ml) was treated, at once, with the dioxo compound, from Example 1, (2.8 g, 15.6 mmol). The solution was warmed to 80° C. and stirred, under $N_2$ atmosphere, for one hour. This solution was then treated, at once, with n-propyliodide (7.75 g, 46 mmol). This solution was stirred at 80° C. for 24 hours. The DMF was removed in vacuo to give an oily residue. The residue was suspended in water (100 ml) and extracted with chloroform (5×100ml). The chloroform solution was dried over magnesium sulfate and the solvent removed in vacuo to give a thick yellow oil, yield 1.85 g of 1,3-dimethyl-4,6-dipropyl-1H-pyra-3-zolo[4,3-d]pyrimidine-5,7-[4H,6H]dione (45%).

Analysis as: $C_{13}H_{20}N_9O_2$: Calcd: C, 59.07; H, 7.63; N, 21.20. Found: C, 59.29; H, 7.79; N, 20.90.

I claim:
1. A compound having the formula:

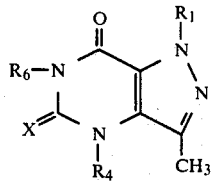

I wherein X is oxygen or sulfur; $R_1$ is lower alkyl of from one to six carbons, inclusive, lower alkenyl of from two to six carbons, hydroxyalkyl from one to six carbons, inclusive, hydroxyalkenyl of from two to six carbons, inclusive, aminoalkyl of from one to six carbons, inclusive, or aminoalkenyl of from two to six carbons, inclusive; $R_4$ is hydrogen, lower alkyl of from one to six carbons, inclusive, lower alkenyl of from two to six carbons, inclusive, hydroxyalkyl of from one to six carbons, inclusive, hydroxyalkenyl of from two to six carbons, inclusive, aminoalkyl of from one to six carbons, inclusive, or aminoalkenyl of from two to six carbons, inclusive, $R_6$ is hydrogen, lower alkyl of from one to six carbons, inclusive, alkenyl of from two to six carbons, inclusive; hydroxyalkyl of from one to six carbons, inclusive, hydroxyalkenyl of from two to six carbons, inclusive, or aminoalkenyl of from two to six carbons, inclusive; and the pharmaceutically acceptable salts thereof.

2. A compound of claim 1 wherein X is oxygen.

3. A compound of claim 2 wherein $R_1$ is alkyl.

4. A compound of claim 3 wherein $R_1$ is ethyl and $R_4$ is hydrogen.

5. A compound of claim 4 wherein the embodiment is 1H-1-ethyl-3-methyl-6-propylpyrazolo[4,3d]pyrimidine-5,7-[4H,6H]dione.

6. A compound of claim 3 wherein the embodiment is 1,3-dimethyl-1H-pyrazolo[4,3-d]pyrimidine-5,7-[4H,6H]dione.

7. A compound of claim 4 wherein the embodiment is 1-ethyl-3-methyl-1H-pyrazolo[4,3-d]pyrimidine-5,7-[4H,6H]dione.

8. A compound of claim 4 wherein the embodiment is 1-ethyl-3-methyl-6-ethyl-1H-pyrazolo[4,3-d]pyrimidine-5,7-[4H,6H]dione.

9. A compound of claim 4 wherein the embodiment is 1-ethyl-3,6-dimethyl-1H-pyrazolo[4,3-d]pyrimidine-5,7-[4H,6H]dione.

10. A compound of claim 3 wherein the embodiment is 1,3,4,6-tetramethyl-1H-pyrazolo[4,3-d]pyrimidine-5,7-[4H,6H]dione.

11. A compound of claim 4 wherein the embodiment is 4,6-diethyl-1,3-dimethyl-1H-pyrazolo[4,3-d]pyrimidine-5,7-[4H,6H]dione.

12. A compound of claim 3 wherein the embodiment is 1,3-dimethyl-4,6-dipropyl-1H-pyrazolo[4,3-d]-pyrimidine-5,7-[4H,6H]dione.

13. A compound of claim 1 wherein the embodiment is 1-ethyl-1,4,5,6-tetrahydro-3-methyl-pyrazolo[4,3-d]pyrimidine-5-thione-7one.

14. A pharmaceutical composition for treating bronchoconstriction or cardiac insufficiency comprising bronchodilating or cardiac stimulating and cardiotonic effective amount of a compound according to claim 1 in admixture with a pharmaceutically acceptable carrier.

15. A method for treating cardiac insufficiency in a mammal suffering therefrom comprising administering to such mammal a compound as claimed in claim 1 in unit dosage form.

16. A method for treating bronchoconstriction in a mammal suffering therefrom comprising administering to such mammal a compound as claimed in claim 1 in unit dosage form.

* * * * *